United States Patent [19]

Manzer et al.

[11] Patent Number: 5,008,476

[45] Date of Patent: Apr. 16, 1991

[54] PROCESS FOR THE PREPARATION OF 1,1,1,2-TETRAFLUOROETHANE

[75] Inventors: Leo E. Manzer; V. N. Mallikarjuna Rao, both of Wilmington, Del.

[73] Assignee: E. I. du Pont de Nemours and Company, Wilmington, Del.

[21] Appl. No.: 449,407

[22] Filed: Dec. 18, 1989

Related U.S. Application Data

[63] Continuation of Ser. No. 262,298, Oct. 25, 1988, abandoned.

[51] Int. Cl.$^5$ .................... C07C 17/10; C07C 19/08; C07C 17/20
[52] U.S. Cl. .................................. 570/176; 570/163; 570/166; 570/170; 570/175
[58] Field of Search ............... 570/166, 176, 163, 170, 570/175

[56] References Cited

U.S. PATENT DOCUMENTS 4,605,798  8/1986  Abel et al. .

FOREIGN PATENT DOCUMENTS 117580  1/1976  German Democratic Rep. .
1578933  11/1980  United Kingdom .

OTHER PUBLICATIONS

Vecchio et al., J. Fluorine Chem., 4, 117-139 (1974).
Gervasutti et al., J. Fluorine Chem., 19, 1-20 (1981).

Primary Examiner—Alan Siegel

[57] ABSTRACT

Improved process for the preparation of 1,1,1,2-tetrafluoroethane by the steps of chlorofluorination of selected organic compounds using $Cl_2$ and HF followed by hydrogenolysis of the resulting products, the improvement residing in the use of excess HF and recycle of the unreacted compounds and byproducts to the chlorofluorination step.

20 Claims, No Drawings

PROCESS FOR THE PREPARATION OF 1,1,1,2-TETRAFLUOROETHANE

This application is a continuation of application Ser. No. 07/262,298 filed Oct. 25, 1988 now abandoned.

FIELD OF THE INVENTION

Improved process for the preparation of 1,1,1,2-tetrafluoroethane (FC-134a) by chlorofluorination of selected organic compounds in the presence of excess HF followed by hydrogenolysis of the resulting products.

BACKGROUND OF THE INVENTION

East German Patent 117,580 discloses a process for preparing a fluorinated alumina catalyst in the presence of promoter metals from an activated alumina, and its use for fluorinating two-carbon compounds in the gas phase. Asymmetrical $C_2$ fluorocarbons and pentafluorochloroethane (FC-115) are claimed to be prepared by this process using a molar ratio of tetrachloroethylene/chlorine/hydrogen fluoride of 1/1/3 to 1/1/5.1. Pentafluorochloroethane concentrations ranged from 6% to 57% of the products at 350° C. and 8.5 s contact time, and at 450° C. and 7.3 s contact time, respectively.

Vechhio, M. et. al., J. Fluorine Chem., 4, 117-39 (1974) describe the chlorofluorination of tetrachloroethylene using $Cl_2$ and HF at ca. 400° C. in the presence of an aluminum fluoride catalyst to yield the asymmetrical isomers of dichlorotetrafluoroethane and trichlorotrifluoroethane as the major products. In another experiment a 1/1 molar mixture of $CCl_2FCClF_2$(FC-113)/HF was passed over an $AlF_3$ catalyst at 400° C., and 10.3 mol % FC-115 and 2.5 mol % $C_2Cl_4F_2$ (FC-112 and FC112a) were obtained. In a comparable experiment using a 1/1 FC-113/$N_2$ molar mixture, 6.8 mol % FC-115 and 8.8 mol % $C_2Cl_4F_2$ (FC-112 and FC-112a) were observed. The FC-115 concentration is dependent on both the HF concentration and disproportionation reactions, while the FC-112s concentration is dependent only on disproportionation reactions. The FC-112s concentration when HF was in the feed suggest that disproportionation reactions are occurring to a significant extent when the HF/FC-113 molar ratio is 1/1; additionally, more FC-115 was observed with HF in the feed.

U.S. Pat. No. 4,605,798 discloses a process for the preparation of trichlorotrifluoroethane, dichlorotetrafluoroethane, and monochloropentafluoroethane by the reaction of chlorine, HF, and tetrachloroethylene over a variety of catalysts, some of which are claimed to be oxides or halides of aluminum. FC-115 is disclosed to be produced in a fluorination-dismutation (i.e., disproportionation) zone by the reactions of HF and dichlorotetrafluoroethane. Furthermore, the amount of asymmetrical isomer $CF_3CCl_2F$ (FC-114a) produced is claimed to comprise less than 7% of the dichlorotetrafluoroethane products GB 1,578,933 claims a process for the preparation of 1,1,1,2-tetrafluoroethane (FC-134a) or 1,1,2,2-tetrafluoroethane (FC-134) by hydrogenating a haloethane having four or five fluorine atoms of formula $CF_2XCFYZ$ where X is fluorine or chlorine; and when X is fluorine, Y is chlorine or fluorine; and when Y is chlorine Z is chlorine, fluorine or hydrogen; and when Y is fluorine Z is hydrogen; and when X is chlorine Y is fluorine and Z is either chlorine or hydrogen, over a supported Pd catalyst at a temperature of 200° C. to 450° C. In example 7 it is seen that in order to convert all of the intermediate 1,1,1,2-tetrafluoro-2-chloroethane (FC-124) to FC-134a a hydrogenolysis temperature of greater than 350° C. is required.

Gervasutti, C. et. al., J. Fluorine Chem., 19, 1-20 (1981) disclose a process for the preparation of FC-134a from isomeric mixtures of dichlorotetrafluoroethanes through selective hydrogenolysis of 1,1,1,2-tetrafluoro-2,2-dichloroethane (FC-114a) catalyzed by Pd/C. The 1,1,2,2-tetrafluoro-1,2-dichloroethane (FC-114) was more stable toward hydrogenolysis. The concentration of FC-134a, from FC-114a hydrogenolysis, in the reaction products is shown to increase up to a maximum temperature of about 200° C. above which its concentration decreases.

This invention provides a multi-step process with recycle for preparing 1,1,1,2-tetrafluoroethane (FC-134a), useful as a refrigerant, in very high yield by minimizing the formation of $CF_3CClF_2$ (FC-115) via disproportionation of $C_2Cl_2F_4$ (FC-114 and FC-114a), without suppressing the isomerization of $CClF_2CClF_2$ (FC-114) to $CF_3CCl_2F$ (FC-114a).

SUMMARY OF THE INVENTION

The present invention provides an improvement in the process for the preparation of 1,1,1,2-tetrafluoroethane by
  (a) reacting at least one compound of the formula $C_2Cl_{4-x}Z_x$ or $C_2Cl_{6-y}Z_y$ wherein x=0 to 4, y=0 to 6, and Z is at least one of hydrogen or fluorine and wherein the total number of fluorine atoms in the compound is $\leq 3$, in the gaseous phase with chlorine in at least the stoichiometric amount needed to convert $C_2Cl_{4-x}Z_x$ and/or $C_2Cl_{6-y}Z_y$ to $C_2Cl_2F_4$, and with HF, at a temperature of about 300° C. to about 450° C., in the presence of at least one catalyst selected from fluorinated alumina or $AlF_3$ to produce 1,1,1,2-tetrafluorodichloroethane (FC-114a), 1,1,2,2-tetrafluorodichloroethane (FC-114) and pentafluorochloroethane (FC-115); and
  (b) contacting the FC-114a and FC-114 produced in (a) in the gaseous phase with $H_2$ at a temperature of about 100° C. to about 350° C. in the presence of a hydrogenolysis catalyst to produce a gaseous mixture comprising 1,1,1,2-tetrafluoroethane (FC-134a), unreacted FC-114 and FC-114a, 1,1,1,2-tetrafluorochloroethane (FC-124), 1,1,1-trifluoroethane (FC-143a), and unreacted pentafluorochloroethane (FC-115).

One aspect of the improvement resides in utilizing an amount of HF in (a) in at least 0.5 moles in excess of the stoichiometric amount needed to convert $C_2Cl_{4-x}Z_x$ and/or $C_2Cl_{6-y}Z_y$ to $C_2Cl_2F_4$. The excess HF has the beneficial effect of suppressing the disproportionation of FC-114a and/or FC-114, which results in the formation of unwanted FC-115. In addition the excess HF does not inhibit the isomerization of FC-114 to FC-114a, which is necessary to high yield production of FC-134a from the hydrogenolysis in (b). Because the presence of excess HF eliminates any substantial formation of FC-115, which if recycled to (a) could represent a yield loss by reacting to form hexafluoroethane, a further improvement resides in the additional step (c) of recycling the unreacted FC-114 and FC-114a, FC-124 and FC-143a from (b) to step (a) for the production of additional FC-114a. Note that in the practice of this invention because of the excess HF, isomerization of FC-114 to FC-114a, which is converted to FC-134a, is not inhibited.

When the reaction temperature of (b) is less than about 350° C., the FC-124 byproduct cannot be recycled to (b) because the complete hydrogenolysis of FC-124 to FC-134a requires a temperature higher than about 350° C. The direct hydrogenolysis of FC-124 in the above process would require an additional hydrogenator, thereby adding to the cost and the complexity of the process. Another penalty of operating the hydrogenolysis reactor at temperatures above about 200° C. is the decrease in yield of the desired product FC-134a.

With control of disproportionation and recycle in accordance with this invention, the overall yield of FC-134a is over 95%. Using conventional methods which lack the control of disproportionation and recycle, the overall yield of FC-134a is less than 80%.

DETAILS OF THE INVENTION

The starting compounds useful in the process of this invention defined by the formula $C_2Cl_{4-x}Z_x$ wherein $x=0$ to 4 and Z is hydrogen, fluorine, or a combination of hydrogen and fluorine with the proviso that the total number of fluorine atoms in the molecule is $\leq 3$, preferably include $x=4$ and $Z=H$, i.e., $CH_2=CH_2$; $x=4$ and $Z=F$ and H, i.e., $CHF=CH_2$, $CF_2=CH_2$, $CHF=CHF$, and $CF_2=CHF$; $x=3$ and $Z=H$, i.e., $CHCl=CH_2$; $x=3$ and $Z=H$ and F, e.g., $CFCl=CH_2$, $CHCl=CHF$, $CFCl=CHF$; $x=3$ and $Z=F$, i.e., $CFCl=CF_2$; $x=2$ and $Z=H$, i.e., $CCl_2=CH_2$, and $CHCl=CHCl$; $x=2$ and $Z=F$ and H, i.e., $CCl_2=CHF$ and $CFCl=CHCl$; $x=2$ and $Z=F$, i.e., $CCl_2=CF_2$ and $CFCl=CFCl$; $x=1$ and $Z=H$, i.e., $CCl_2-CHCl$; $x=1$ and $Z=F$, i.e., $CCl_2=CFCl$; and $x=0$, i.e., $CCl_2=CCl_2$.

The starting compounds useful in the process of this invention defined by the formula $C_2Cl_{6-y}Z_y$ wherein $y=0$ to 6 and Z is hydrogen, fluorine or a combination of hydrogen and fluorine with the proviso that the total number of fluorine atoms in the molecule is $\leq 3$, preferably include $y=6$ and $Z=H$, i.e., $CH_3CH_3$; $y=6$ and $Z=F$ and H, i.e., $CH_2FCH_3$, $CHF_2CH_3$, $CH_2FCH_2F$, $CHF_2CH_2F$, $CF_3CH_3$; $y=5$ and $Z=H$, i.e., $CH_3CHClF$, $CH_2FCH_2Cl$, $CH_3CClF_2$, $CHF_2CH_2Cl$, $CH_2FCHClF$, $CF_3CH_2Cl$, $CHF_2CHClF$, and $CH_2FCF_2Cl$; $y=4$ and $Z=H$, i.e., $CH_3CHCl_2$; $y=4$ and $Z=F$ and H, i.e., $CH_2FCHCl_2$, $CH_2FCCl_2F$, $CHClFCH_2Cl$, $CClF_2CH_2Cl$, $CHF_2CHCl_2$, $CF_3CHCl_2$, $CHF_2CFCl_2, CH_2ClCH_2Cl$, $CHClFCHClF$, and $CClF_2CHClF$; $y=3$ and $Z=H$, i.e., $CH_3CCl_3$ and $CHCl_2CH_2Cl$; $y=3$ and $Z=F$ and H, i.e., $CCl_3CH_2F$, $CCl_3CHF_2$, $CFCl_2CH_2Cl$, $CHCl_2CHClF$, $CHCl_2CF_2Cl$, $CFCl_2CHClF$, and $CFCl_2CF_2Cl$; $y=3$ and $Z=F$, i.e., $CCl_3CF_3$; $y=2$ and $Z=H$, e.g., $CCl_3CH_2Cl$; $y=2$, $Z=F$ and H, e.g., $CCl_3CHClF$; $y=2$ and $Z=F$, i.e., $CCl_3CClF_2$; $y=1$ and $Z=H$, i.e., $CCl_3CHCl_2$; $y=1$ and $Z=F$, i.e., $CCl_3CCl_2F$; and $y=0$, i.e., $CCl_3CCl_3$.

Mixtures of any of the above compounds can be used. Tetrachloroethylene is especially preferred.

The reaction of the starting compound or compounds with HF and $Cl_2$ in the presence of fluorinated alumina or $AlF_3$, is conducted at about 300° C. to 450° C., preferably about 325° C. to 400° C., and most preferably about 350° C. to 375° C.

The contact time can vary widely depending on the degree of conversion desired and generally will be about 1 to 60 seconds, preferably about 15 to 30 seconds at atmospheric pressure.

The amount of HF should be at least 0.5, preferably at least 1.0 moles, and more preferably at least 2.0 moles, in excess of the stoichiometric amount needed to convert $C_2Cl_{4-x}Z_x$ or $C_2Cl_{6-y}Z_y$ to $C_2Cl_2F_4$ (FC-114 and FC-114a), in order to effectively control disproportionation reactions. When the starting compound is $CCl_2=CCl_2$, the molar ratio of HF to $CCl_2=CCl_2$ can range from about 4.5/1 to 10/1, preferably about 5/1 to 10/1 and more preferably about 6/1 to 7/1. The HF may be diluted with inert materials if so desired. Such inert materials which are suitable for the process of this invention include nitrogen, helium or argon.

The amount of $Cl_2$ should be at least the stoichiometric amount needed to convert $C_2Cl_{4-x}Z_x$ or $C_2Cl_{6-y}Z_y$ to $C_2Cl_2F_4$. Generally, the molar ratio of $Cl_2$ to $CCl_2=CCl_2$ can range from about 1/1 to 10/1.

The reaction of the starting compound or compounds with HF/$Cl_2$ may be conducted in any suitable reactor, including fixed and fluidized bed reactors. The reaction vessel should be constructed from materials which are resistant to the corrosive effects of hydrogen fluoride and chlorine such as Hastelloy ® and Inconel ®.

The reaction mixture comprising FC-114a and FC-114, prepared as described above, is contacted with hydrogen in the presence of palladium on carbon, at about 100° C. to 230° C., in any suitable reactor, including fixed and fluidized bed reactors. The reaction vessel should be constructed from materials which are resistant to the corrosive effects of hydrogen halides.

The contact time can vary widely depending on the degree of conversion desired and generally will be about 1 to 60 seconds, preferably about 10 to 30 seconds.

Generally, the molar ratio of $H_2$ to 1,1,1,2-tetrafluorodichloroethane can range from about 0.5/1 to 20/1, preferably about 0.5/1 to 10/1 and more preferably about 1/1 to 3/1. During the course of the reaction unreacted FC-114a, FC-114, FC-124 and FC-143a can be recycled to the initial contacting step, after separating the desired product FC-134a.

Pressure is not critical in either the reaction with HF and $Cl_2$ or the subsequent hydrogenolysis. Atmospheric and superatmospheric pressures are the most convenient and are therefore preferred.

EXAMPLES

In the following illustrative examples of the invention, parts and percentages are by weight and temperatures are in degrees Celsius unless otherwise specified. All product compositions are given in area percent.

General Procedure for Chlorofluorination

5 The reactor (0.5 inch ID by 12 inch length Inconel ® pipe) was charged with alumina or aluminum fluoride as described in the following examples and placed in a sand bath. The bath was gradually heated to 400° C. while $N_2$ at 50 cc/min was passed through the reactor to remove traces of water. When the reactor charge was alumina, the temperature was lowered and maintained at about 200° C. while HF and $N_2$ (¼ molar ratio) was passed through the reactor, and then slowly decreasing the $N_2$ flow until only HF was being passed through the reactor. At this point, the temperature was gradually raised to 450° C. and maintained there for 15 to 300 minutes. The HF treatment converts alumina to fluorinated alumina. When the reactor charge was aluminum fluoride, this last process step is omitted.

The temperature was then adjusted to the indicated values followed by initiation of flow of the halogenated ethane or ethylene derivative. All flows were adjusted to give the indicated molar ratios and contact times in the Examples.

The reactor effluent was sampled on-line with a Hewlett Packard HP 5890 gas chromatograph using a 20'×⅛' column containing Krytox® on an inert support and helium flow of 35 cc/min. Analysis conditions were 70° C. for 3 min. followed by temperature programming to 180° C. at a rate of 6°/minute.

General Procedure for Hydrogenolysis

A tubular reactor of stainless steel or Hastelloy®, ¼" to ¾" OD, was charged with the desired catalyst. Hydrogen, 25 cc/min was passed through the reactor and the temperature was increased to 300° C. at a rate of 0.5°/min and held at 300° C. for 3 h. The reactor temperature was then reduced to the desired temperature and $H_2/C_2F_4Cl_2$ at the specified ratio was passed over the catalyst.

EXAMPLE 1

Chlorofluorination of $CCl_2=CCl_2$

The general procedure for chlorofluorination was followed using $AlF_3$ (15.7 g, 25 mL, 12–20 mesh). The reaction temperature was 375° C., the mol ratio of $HF/C_2Cl_4/Cl_2$ was 5/1/1 and the contact time was 15 s. The composition of the product stream was 0.5% $CF_3CClF_2$, 0.8% $CClF_2CClF_2$, 49.2% $CF_3CCl_2F$, 0.7% $CF_3CHCl_2$, 3.2% $CCl_2FCClF_2$, 12.9% $CF_3CCl_3$, 0.1% $CClF_2CHCl_2$, 0.6% $CClF=CCl_2$, 1.1% $CCl_2FCCl_2F$, 0.3% $CCl_2FCCl_3$, and 30.5% $CCl_2=CCl_2$.

The yield (based on $CCl_2=CCl_2$ converted) of $CF_3CCl_2F$ was 70.8%.

EXAMPLE 2

Chlorofluorination of $CCl_2=CCl_2$

The procedure and the $AlF_3$ catalyst were the same as used in Example 1. The reaction temperature was 375° C., the mol ratio of $HF/C_2Cl_4/Cl_2$ was 5/1/1 and the contact time was 30 s. The composition of the product stream was 1.0% $CF_3CClF_2$, 1.2% $CClF_2CClF_2$, 58.8% $CF_3CCl_2F$, 0.9% $CF_3CHCl_2$, 1.6% $CCl_2FCClF_2$, 9.4% $CF_3CCl_3$, 0.1% $CClF_2CHCl_2$, 0.9% $CClF=CCl_2$, 0.5% $CF_2ClCCl_3$, 0.2% $CCl_2FCCl_3$, and 25.4% $CCl_2=CCl_2$.

The yield (based on $CCl_2=CCl_2$ converted) of $CF_3CCl_2F$ was 78.8%.

EXAMPLE 3

Hydrogenolysis of $CF_3CCl_2F$ (FC-114a) to $CF_3CH_2F$

The general procedure for hydrogenolysis was followed using as catalyst 0.5% Pd/C (5.0 g) at a hydrogen pressure of 446 KPa. The other reaction conditions, and products are shown in Table 1.

TABLE 1

| | | Hydrogenolysis of $CF_3CCl_2F$ (FC-114a) | | | | | |
|---|---|---|---|---|---|---|---|
| Exp. | Cat. Temp. °C. | FC-114a Flow mL/h | $H_2$ Flow cc/min | FC-114a % Conv. | $CF_3CH_2F$ % Yield | $CF_3CFHCl$ % Yield | $CF_3CH_3$ % Yield |
| A | 150 | 1.0 | 4.83 | 61.1 | 46.9 | 6.7 | 2.8 |
| B | 149 | 2.0 | 13.76 | 53.8 | 40.3 | 6.6 | 2.5 |
| C | 174 | 1.0 | 6.84 | 97.3 | 75.5 | 13.5 | 4.1 |
| D | 174 | 2.0 | 13.77 | 89.5 | 68.6 | 10.8 | 4.7 |
| E | 175 | 4.0 | 27.60 | 81.3 | 62.5 | 9.2 | 4.9 |
| F | 174 | 2.0 | 9.98 | 76.7 | 59.5 | 7.7 | 4.9 |
| G | 226 | 4.0 | 25.09 | 98.5 | 68.3 | 11.6 | 13.7 |

EXAMPLE 4

Chlorofluorination of $CF_3CHClF$

The procedure and the $AlF_3$ catalyst were the same as used in Examples 1 and 2. The reaction temperature was 375° C., the mol ratio of $HF/CF_3CHClF/Cl_2$ was 1/1/1.5 and the contact time was 30 s. The composition of the reaction effluent was 7.3% $CF_3CClF_2$, 2.5% $CClF_2ClF_2$, 54.5% $CF_3CCl_2F$, 5.0% $CF_3CHCl_2$, 0.6% $CCl_2FCClF_2$, 6.4% $CF_3CCl_3$, 2.0% $CF_3CHF_2$, 0.5% $CF_2HCF_2Cl$, 0.1% $CCl_2FCCl_2F$, and 21.1% $CF_3CHClF$.

The yield (based on $CF_3CHClF$ converted) of $CF_3CCl_2F$ was 69.1%.

EXAMPLE 5

Chlorofluorination of $CF_3CH_3$

The procedure and the $AlF_3$ catalyst were the same as used in Examples 1, 2 and 4. The reaction temperature was 350° C., the mol ratio of $HF/CF_3CH_3/Cl_2$ was 2/1/4 and the contact time was 20 s. The composition of the product stream was 1.2% $CF_3CClF_2$, 2.1% $CClF_2CClF_2$, 59.5% $CF_3CCl_2F$, 12.8% $CF_3CHCl_2$, 2.5% $CCl_2FCClF_2$, 18.9% $CF_3CCl_3$, 1.2% $CF_3CHClF$, 0.8% $CF_3CH_2Cl$, and 0.7% $CF_{ClCCl_3}$.

The yield (based on $CF_3CH_3$ converted) of $CF_3CCl_2F$ was 59.5%.

EXAMPLE 6

Isomerization of $CClF_2CClF_2$ a. The procedure and the $AlF_3$ catalyst were the same as used in Examples 1, 2, 4 and 5. The $CClF_2CClF_2$ feed contained about 9% $CF_3CCl_2F$. The reaction temperature was 375° C., the mol ratio of $HF/CClF_2CClF_2/N_2$ was 0/1/2 and the contact time was 30 s. The composition of the product stream was 31.4% $CF_3CClF_2$, 2.2% $CClF_2CClF_2$, 18.2% $CF_3CCl_2F$, 3.0% $CCl_2FCClF_2$, 36% $CF_3CCl_3$, 4.4% $CCl_3CClF_2$, 0.8% $CCl_3CCl_2F$, and 3.9% $CCl_2=CCl_2$.

The large concentrations of $CF_3CClF_2$, $CF_3CCl_3$, and $CCl_2FCClF_2$ indicate that a significant amount $C_2Cl_2F_4$ has disproportionated.

b. The above experiment was repeated at 425° C. with mol ratios of $HF/CClF_2CClF_2/N_2$ of 6/1/0 and a contact time of 15 s. The composition of the product stream was 10.9% $CF_3CClF_2$, 38.7% $CClF_2CClF_2$, 50.2% $CF_3CCl_2F$, and 0.2% $CF_3CCl_2F$.

These results show clearly the inhibiting effect of HF on $C_2Cl_2F_4$ disproportionation while simultaneously not affecting the isomerization of $CClF_2CClF_2$ to $CF_3CCl_2F$.

What is claimed:

1. In a process for preparing 1,1,1,2-tetrafluoroethane which includes the steps of
  (a) reacting at least one two-carbon compound selected from the group consisting of compounds having the formula $C_2Cl_{4-x}Z_x$ and compounds having the formula $C_2Cl_{6-y}Z_y$ wherein x=0 to 4, y=0 to 6, and Z is at least one of hydrogen or fluorine and wherein the total number of fluorine atoms in the compound is $\leq 3$, in the gaseous phase with chlorine in at least the stoichiometric amount needed to convert each of said two carbon compounds to $C_2Cl_2F_4$, and with HF, to produce a mixture comprising 1,1,1,2-tetrafluorodichloroethane, 1,1,2,2-tetrafluorodichloroethane and pentafluorochloroethane; and
  (b) contacting the mixture produced in (a) in the gaseous phase with $H_2$ at a temperature of about 100° C. to about 350° C. in the presence of hydrogenolysis catalyst to produce a gaseous mixture comprising 1,1,1,2-tetrafluorochloroethane, unreacted 1,1,2,2-tetrafluorodichloroethane, and 1,1,1,2-tetrafluorodichloroethane, 1,1,1,2-tetrafluorochloroethane, 1,1,1-trifluoroethane, and unreacted pentafluorochloroethane, an improvement comprising:
  (i) in step (a) reacting said at least one two-carbon compound with HF in excess of the stoichiometric amount needed to fluorinate each of said two-carbon compounds to $C_2Cl_2F_4$ for a time sufficient to produce a product comprising 1,1,1,2-tetrafluorodichloroethane and 1,1,2,2-tetrafluorodichloroethane, said reaction being conducted at a temperature of from about 300° C. to about 450° C. and in the presence of at least one catalyst selected from fluorinated alumina and $AlF_3$ which are suitable for both the isomerization of 1,1,2,2-tetrafluorodichloroethane to 1,1,1,2-tetrafluorodichloroethane and the formation of pentafluorochloroethane by disproportionation of $C_2Cl_2F_4$; and
  (ii) in step (a) utilizing as said excess HF an effective amount of HF, at least about 1 mole in excess of said stoichiometric amount needed to fluorinate the two-carbon compounds to $C_2Cl_2F_4$, to inhibit said disproportionation without suppressing said isomerization.

2. In a process for preparing 1,1,1,2-tetrafluoroethane which includes the steps of
  (a) reacting at least one two-carbon compound selected from the group consisting of compounds having the formula $C_2Cl_{4-x}Z_x$ and compounds having the formula $C_2Cl_{6-y}Z_y$ wherein x=0 to 4, y=0 to 6, and Z is at least one of hydrogen or fluorine and wherein the total number of fluorine atoms in the compound is $\leq 3$, in the gaseous phase with chlorine in at least the stoichiometric amount needed to convert each of said two carbon compounds to $C_2Cl_2F_4$, and with HF, to produce a mixture comprising 1,1,1,2-tetrafluorodichloroethane, 1,1,2,2-tetrafluorodichloroethane and pentafluorochloroethane; and
  (b) contacting the mixture produced in (a) in the gaseous phase with $H_2$ at a temperature of about 100° C. to about 350° C. in the presence of a hydrogenolysis catalyst to produce a gaseous mixture comprising 1,1,1,2-tetrafluoroethane, unreacted 1,1,2,2-tetrafluorodichloroethane, and 1,1,1,2-tetrafluorodichloroethane, 1,1,1,2-tetrafluorochloroethane, 1,1,1-trifluoroethane, and unreacted pentafluorochloroethane, an improvement comprising:
  (i) in step (a) reacting said at least one two-carbon compound with HF in excess of the stoichiometric amount needed to fluorinate each of said two-carbon compounds to $C_2Cl_2F_4$ for a time sufficient to produce a product comprising 1,1,1,2-tetrafluorodichloroethane and 1,1,2,2-tetrafluorodichloroethane, said reaction being conducted at a temperature of from about 300° C. to about 450° C. and in the presence of at least one catalyst selected from fluorinated alumina and $AlF_3$ which are suitable for both the isomerization of 1,1,2,2-tetrafluorodichloroethane to 1,1,1,2-tetrafluorodichloroethane and the formation of pentafluorochloroethane by disproportionation of $C_2Cl_2F_4$;
  (ii) in step (a) utilizing as said excess HF an effective amount of HF, at least about 0.5 mole in excess of said stoichiometric amount needed to fluorinate the two-carbon compounds to $C_2Cl_2F_4$, to inhibit said disproportionation; and
  (iii) further including the steps of separating 1,1,1,2-tetrafluoroethane from the gaseous mixture produced in step (b), and then recycling 1,1,1,2-tetrafluorochloroethane and 1,1,1, trifluoroethane as well as 1,1,2,2-tetrafluorodichloroethane and 1,1,1,2-tetrafluorodichloroethane, from the gaseous mixture produced in step (b) to step (a).

3. The process of claim 1 comprising the additional step (c) recycling the unreacted FC-114 and FC-114a, FC-124, and FC-143a from (b) to step (a).

4. The process of claim 3 wherein the two-carbon compound of (a) is tetrachloroethylene.

5. The process of claim 3 wherein the amount of HF is at least 2.0 moles in excess of the stoichiometric amount.

6. The process of claim 3 wherein the temperature in (a) is from about 325° C. to about 400° C.

7. The process of claim 3 wherein the temperature in (a) is from about 350° C. to about 375° C.

8. The process of claim 9 wherein the two-carbon compound of step (a) is tetrachloroethylene.

9. The process of claim 2 wherein the amount of HF is an amount at least 1.0 mole in excess of the stoichiometric amount effective to inhibit said disproportionation without suppressing said isomerization.

10. The process of claim 2 wherein the amount of HF is at least 2.0 moles in excess of the stoichiometric amount.

11. The process of claim 2 wherein the reaction temperature in step (a) is from about 325° C. to about 400° C.

12. The process of claim 2 wherein the reaction temperature in step (a) is from about 350° C. to about 375° C.

13. The process of claim 2 wherein the disproportionation and recycle are controlled to produce an overall yield of 1,1,1,2-tetrafluoroethane of over 95%.

14. The process of claim 13 wherein the two-carbon compound of step (a) is tetrachloroethylene.

15. The process of claim 14 wherein the amount of HF is at least 1.0 mole in excess of the stoichiometric amount.

16. The process of claim 15 wherein the reaction temperature in step (a) is from about 325° C. to about 400° C.

17. The process of claim 13 wherein the amount of HF is at least 1.0 mole in excess of the stoichiometric amount.

18. The process of claim 13 wherein the amount of HF is at least 2.0 moles in excess of the stoichiometric amount.

19. The process of claim 13 wherein the reaction temperature in step (a) is from about 325° C. to about 400° C.

20. The process of claim 19 wherein the reaction temperature in step (a) is from about 350° C. to about 357° C.

* * * * *